United States Patent
Suzuki et al.

(10) Patent No.: US 6,762,303 B2
(45) Date of Patent: Jul. 13, 2004

(54) METHOD FOR PRODUCING PYRIDINE COMPOUNDS

(75) Inventors: Ryo Suzuki, Minami-ashigara (JP); Katsuyoshi Yamakawa, Minami-ashigara (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 31 days.

(21) Appl. No.: 09/960,327

(22) Filed: Sep. 24, 2001

(65) Prior Publication Data

US 2002/0065420 A1 May 30, 2002

(30) Foreign Application Priority Data

Sep. 27, 2000 (JP) ........................................ 2000-295054
Sep. 27, 2000 (JP) ........................................ 2000-295071

(51) Int. Cl.$^7$ .......................................... C07D 213/06
(52) U.S. Cl. ...................................... 546/252; 546/314
(58) Field of Search ................................. 546/252, 314

(56) References Cited

PUBLICATIONS

Kin–ya Akiba et al.; Bull. Chem. Soc. Jpn., 57, 1994–1999 (1984).
Ivan Lantos et al., J. Org. Chem. 1988, 53, 4223–4227.
Dwight D. Weller et al.; J. Org. Chem., 1983, 48, 4597–4605.
Lise–Lotte Gundersen et al., Tetrahedron, vol. 48, No. 27, pp. 5647–5656, 1992.

*Primary Examiner*—Zinna Northington Davis
(74) *Attorney, Agent, or Firm*—Birch, Stewart, Kolasch & Birch, LLP

(57) ABSTRACT

A method for producing a pyridine compound of formula (II), comprising oxidizing a dihydropyridine compound of formula (I) in the presence of (i) at least one acid and at least one nitrous acid or a nitrite, or (ii) at least one base, and a hydrogen peroxide solution:

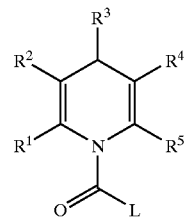

Formula (I)

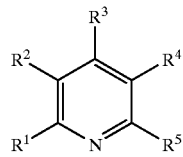

Formula (II)

wherein in formulae (I) and (II), $R^1$ to $R^5$ represents a hydrogen atom, or a substituent; L represents an alkyl group, an alkoxy group, an aryl group, or an aryloxy group.

18 Claims, No Drawings

METHOD FOR PRODUCING PYRIDINE COMPOUNDS

FIELD OF THE INVENTION

The present invention relates to a method for producing a pyridine compound that is useful for photographic additives, sensitizing dyes, pharmaceuticals, organic EL materials, liquid crystal materials, nonlinear optical materials, and so on, or for synthetic intermediates of these materials.

BACKGROUND OF THE INVENTION

Examples of methods for synthesizing pyridine compounds by oxidation of a dihydropyridine compound include an oxidation method using oxygen (as described, for example, in Bull. Chem. Soc. Jpn., 57(7), 1994–1999 (1984); Tetrahedron Lett., 23 (4), 429–432 (1982); and Synth. Commun., 21 (3), 401–406 (1991)); an oxidation method using sulfur (as described, for example, in Chem. Pharm. Bull., 38 (1), 45–48 (1990); J. Org. Chem., 53 (18), 4223–4227 (1988); and JP-A-6-172347 ("JP-A" means unexamined published Japanese patent application)); an oxidation method using o-chloranil (as described, for example, in J. Org. Chem., 48 (24), 4597–4605 (1983); and Heterocycles, 22 (2), 339–344 (1984); and an oxidation method using DDQ (as described, for example, in Tetrahedron, 48 (27), 5647–5656 (1992); and Heterocycles, 45 (3), 434–438 (1997)). However, these methods had disadvantages that the reaction required a long time or high temperature, and moreover, post-treatment, such as removal of a residue, also required much time. Accordingly, it is difficult to say that these methods were suitable for industrial production. Further, these methods were also unsatisfactory as industrial production methods from the viewpoints of cost and environment.

Further, purification techniques, such as chromatography and distillation, have been employed to yield a pyridine compound of high purity. However, the chromatography requires so much chromato-carrier and elution solvent that it is not suitable for industrial production. The distillation also has the problem that it is difficult to purify a pyridine compound having a low melting point or a high boiling point.

SUMMARY OF THE INVENTION

The present invention is a method for producing a pyridine compound represented by formula (II), which comprises oxidizing a dihydropyridine compound represented by formula (I), in the presence of (i) at least one acid and at least one compound selected from the group consisting of nitrous acid and a nitrite, or (ii) at least one base and a hydrogen peroxide solution:

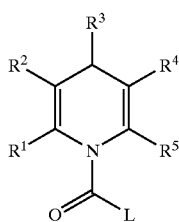

Formula (I)

wherein each of $R^1$ to $R^5$ independently represents a hydrogen atom, or a substituent; L represents an alkyl group, an alkoxy group, an aryl group, or an aryloxy group, each of which may have a substituent:

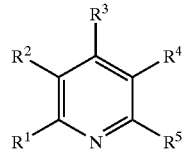

Formula (II)

wherein each of $R^1$ to $R^5$ has the same meanings as those of formula (I).

Further, the present invention is a method for producing the pyridine compound represented by formula (II), which comprises subjecting a crude salt product formed from said pyridine compound and an acid to an active carbon treatment in a solvent containing water, thereby purifying the pyridine compound.

Other and further features and advantages of the invention will appear more fully from the following description.

DETAILED DESCRIPTION OF THE INVENTION

The present invention resides in a producing method of a pyridine compound described below.

(1) A method for producing a pyridine compound represented by formula (II), comprising oxidizing a dihydropyridine compound represented by formula (I), (i) in the presence of at least one acid (in the present specification and the claims, this "acid" mentioned herein means an acid other than nitrous acid and nitrite), and at least one compound selected from the group consisting of nitrous acid and a nitrite, or (ii) in the presence of at least one base and a hydrogen peroxide solution:

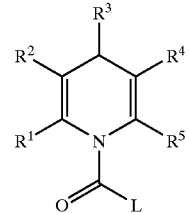

Formula (I)

wherein each of $R^1$ to $R^5$ independently represents a hydrogen atom, or a substituent; L represents an alkyl group, an alkoxy group, an aryl group, or an aryloxy group, each of which may have a substituent:

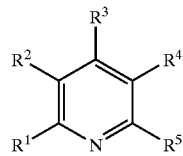

Formula (II)

wherein each of $R^1$ to $R^5$ has the same meanings as those of formula (I).

(2) The method for producing a pyridine compound according to item (1), wherein the reaction is conducted in the presence of at least one acid and at least one compound selected from the group consisting of nitrous acid and a nitrite.

(3) The method for producing a pyridine compound according to item (2), wherein said acid is a carboxylic acid.

(4) The method for producing a pyridine compound according to items (2) or (3), wherein said nitrite is an alkali metal nitrite or an alkaline earth metal nitrite.

(5) The method for producing a pyridine compound according to any one of items (2) to (4), wherein each of $R^1$, $R^2$, $R^4$, and $R^5$ represents a hydrogen atom, and $R^3$ represents an aryl group in formula (I) and formula (II) respectively.

(6) A method for producing a pyridine compound represented by formula (II) described below, comprising subjecting a crude salt product formed from said pyridine compound and an acid to an active carbon treatment in a solvent containing water, thereby purifying the pyridine compound:

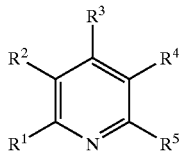

Formula (II)

wherein each of $R^1$ to $R^5$ independently represents a hydrogen atom, or a substituent.

(7) The method for producing a pyridine compound according to item (6), wherein each of $R^1$, $R^2$, $R^4$, and $R^5$ represents a hydrogen atom, and $R^3$ represents an aryl group in formula (II).

(8) The method for producing a pyridine compound according to item (1), wherein the reaction is conducted in the presence of at least one base and a hydrogen peroxide solution.

(9) The method for producing a pyridine compound according to item (8), wherein said base is an inorganic base, or an alkoxide of an alkali metal or alkaline earth metal.

(10) The method for producing a pyridine compound according to the items (8) or (9), wherein each of $R^1$, $R^2$, $R^4$ and $R^5$ in formulae (I) and (II) is a hydrogen atom.

Next, the production method of the present invention will be explained in detail.

The dihydropyridine compound represented by formula (I), which is used in the present invention, and the pyridine compound represented by formula (II), which is produced by the method of the present invention, are explained.

In formulae (I) and (II), each of $R^1$, $R^2$, $R^3$, $R^4$, and $R^5$ independently represents a hydrogen atom, or a substituent. Examples of the substituent include a halogen atom (e.g., fluorine, chlorine, bromine, iodine), an alkyl group (e.g., methyl, ethyl), an aryl group (e.g., phenyl, naphthyl), an alkenyl group (e.g., vinyl), a cyano group, a formyl group, a carboxyl group, an alkoxycarbonyl group (e.g., methoxycarbonyl), an aryloxycarbonyl group (e.g., phenoxycarbonyl), a substituted or unsubstituted carbamoyl group (e.g., carbamoyl, N-phenylcarbamoyl, N,N-dimethylcarbamoyl), an alkyl carbonyl group (e.g., acetyl), an arylcarbonyl group (e.g., benzoyl), a nitro group, a substituted or unsubstituted amino group (e.g., amino, dimethyl amino, anilino), an acylamino group (e.g., acetamido, ethoxycarbonylamino), a sulfonamido group (e.g., methanesulfonamido), an imido group (e.g., succinimido, phthalimido), an imino group (e.g., benzylideneamino), a hydroxyl group, an alkoxy group (e.g., methoxy), an aryloxy group (e.g., phenoxy), an acyloxy group (e.g., acetoxy), an alkylsulfonyloxy group (e.g., methane sulfonyloxy), an arylsulfonyloxy group (e.g., benzenesulfonyloxy), a sulfo group, a substituted or unsubstituted sulfamoyl group (e.g., sulfamoyl, N-phenylsulfamoyl), an alkylthio group (e.g., methylthio), an arylthio group (e.g., phenylthio), an alkylsulfonyl group (e.g., methanesulfonyl), an arylsulfonyl group (e.g., benzenesulfonyl), a silyl group (e.g., dimethylphenylsilyl, triphenylsilyl), a phosphoryl group (e.g., dimethoxyphosphoryl), a heterocyclic group (e.g., 3- to 10-membered saturated or unsaturated heterocyclic group containing at least one of N, O and S atoms, in which sail ring may be a single ring or a condensed ring formed by condensation with another ring; such heterocyclic group is preferably a 5- or 6-membered heterocyclic group, more preferably a 5-membered heterocyclic group containing a nitrogen atom). Besides, the aforementioned substituent may be further substituted with an additional substituent. In case where two or more substituents are involved, they may be the same or different. Further, the substituents which adjoin each other, may combine together to form a ring.

Each of $R^1$, $R^2$, $R^3$, $R^4$, and $R^5$ is preferably a hydrogen atom, a halogen atom, an alkyl group, an aryl group, an alkenyl group, a cyano group, a formyl group, a carboxyl group, an alkoxycarbonyl group, an aryloxycarbonyl group, a substituted or unsubstituted carbamoyl group, an alkylcarbonyl group, an arylcarbonyl group, a nitro group, a substituted or unsubstituted amino group, an acylamino group, a sulfonamido group, a hydroxyl group, an alkoxy group, an aryloxy group, an acyloxy group, a sulfo group, a substituted or unsubstituted sulfamoyl group, an alkylthio group, an arylthio group, an alkylsulfonyl group, an arylsulfonyl group, a silyl group, a phosphoryl group and a heterocyclic group.

Each of $R^1$, $R^2$, $R^3$, $R^4$, and $R^5$ is more preferably a hydrogen atom, a halogen atom, an alkyl group, an aryl group, an alkenyl group, a cyano group, a formyl group, an alkoxycarbonyl group, an aryloxycarbonyl group, a substituted or unsubstituted carbamoyl group, an alkylcarbonyl group, an arylcarbonyl group, a nitro group, an acylamino group, an alkoxy group, an aryloxy group, an acyloxy group, an alkylthio group, an arylsulfonyl group, a silyl group, a phosphoryl group and a heterocyclic group.

For the case of producing a pyridine compound in the presence of a base, a carboxyl group may also be mentioned as a more preferable example of $R^1$ to $R^5$.

Each of $R^1$, $R^2$, $R^3$, $R^4$, and $R^5$ is furthermore preferably a hydrogen atom, a halogen atom, an alkyl group, an aryl group, a cyano group, a formyl group, an alkoxycarbonyl group, an aryloxycarbonyl group, a substituted or unsubstituted carbamoyl group, an alkylcarbonyl group, an arylcarbonyl group, an alkoxy group, an aryloxy group, an acyloxy group, and a heterocyclic group.

For the case of producing a pyridine compound in the presence of a base, a carboxy group may also be mentioned as a furthermore preferable example of $R^1$ to $R^5$.

It is especially preferable that each of $R^1$, $R^2$, $R^4$ and $R^5$ represents a hydrogen atom, and $R^3$ represents an aryl group.

In formula (I), L represents an alkyl group, an alkoxy group, an aryl group, or an aryloxy group, each of which may have a substituent. The alkyl, alkoxy, aryl, or aryloxy group represented by L may be further substituted with a substituent. As the substituent, those substituents exemplified as $R^1$ to $R^5$ may be properly used.

With regard to L, each of the alkyl group and the alkoxy group may be those having preferably 1 to 30 carbon atoms, more preferably 1 to 20 carbon atoms, and furthermore preferably 1 to 15 carbon atoms. They may be branched or may form a ring structure, i.e., they may be a branched alkyl group, a branched alkyloxy group, a cycloalkyl group, or a cycloalkoxy group.

With regard to L, each of the aryl group and the aryloxy group may be those having preferably 6 to 30 carbon atoms, more preferably 6 to 20 carbon atoms, and furthermore preferably 6 to 11 carbon atoms.

Next, specific examples of the compound represented by formula (I) for use in the present invention are shown below. However, the present invention is not limited to these compounds.

(I-1)

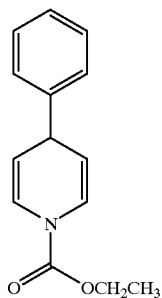

(I-2)

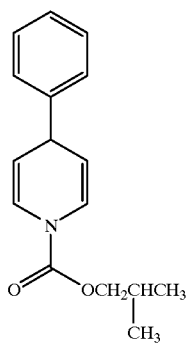

(I-3)

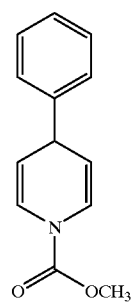

(I-4)

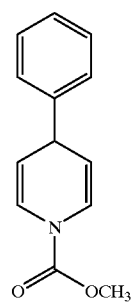

-continued (I-5)

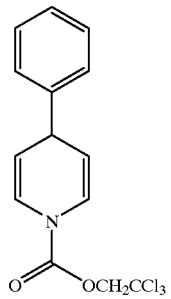

(I-6)

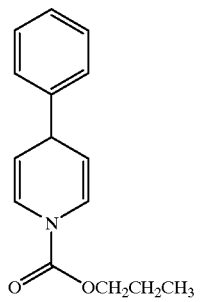

(I-7)

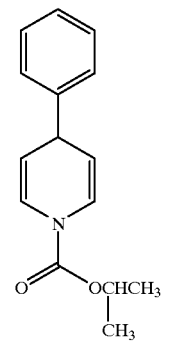

(I-8)

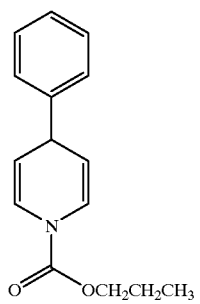

(I-9)

(I-10)
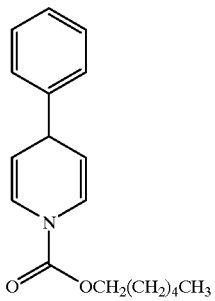
(I-14)
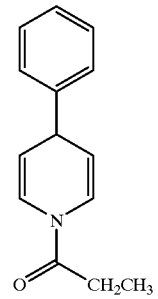
(I-11)
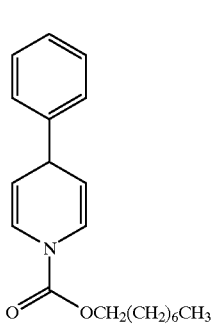
(I-15)
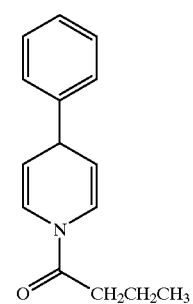
(I-12)
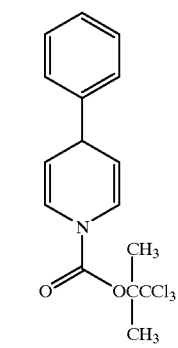
(I-16)
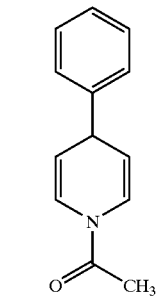
(I-13)
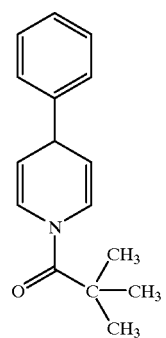
(I-17)

-continued
(I-18)
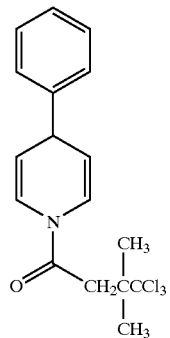
(I-19)
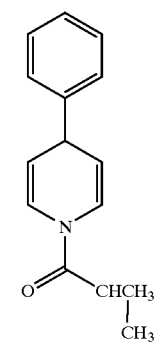
(I-20)
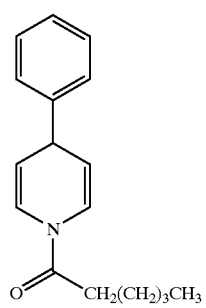
(I-21)
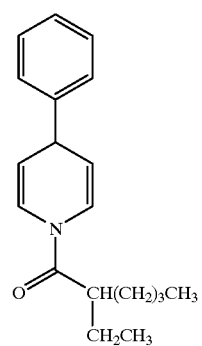
(I-22)
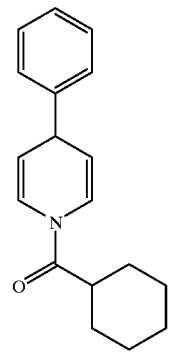
(I-23)
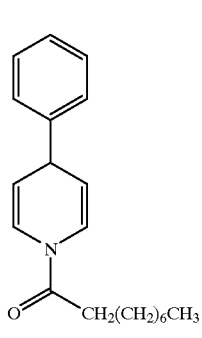
(I-24)
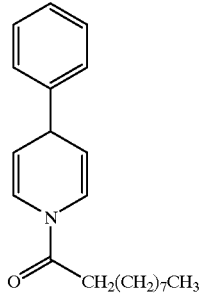
(I-25)
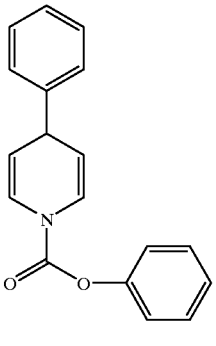

(I-26) 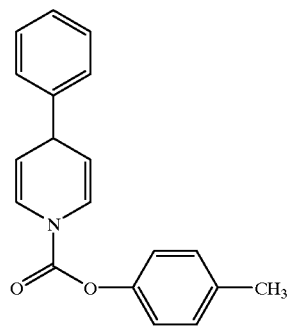
(I-27) 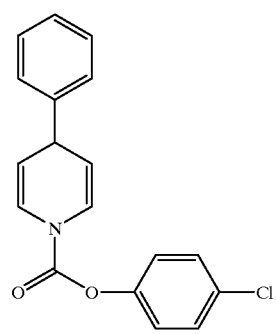
(I-28) 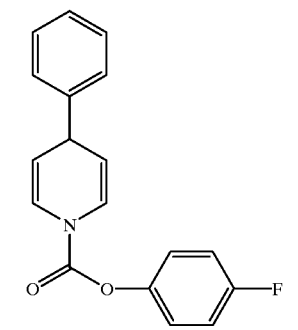
(I-29) 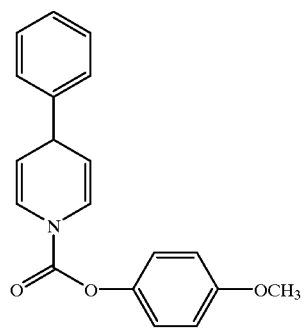
(I-30) 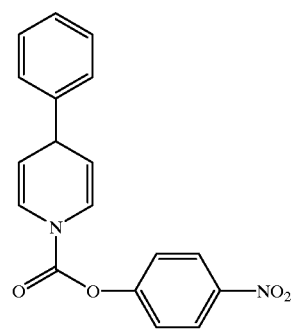
(I-31) 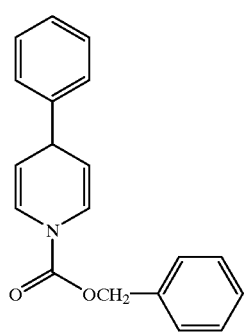
(I-32) 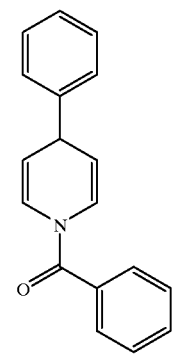
(I-33) 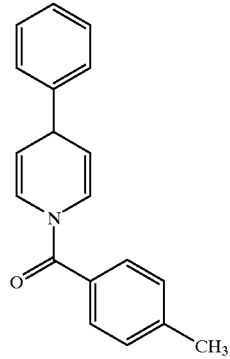

(I-34)
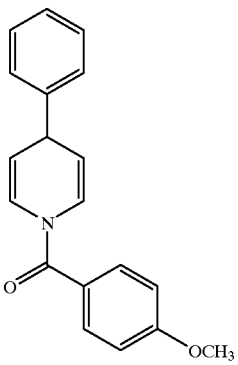
(I-35)
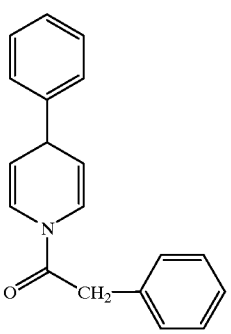
(I-36)
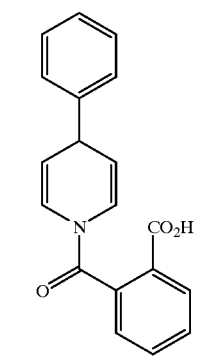
(I-37)
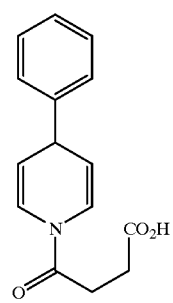
(I-38)
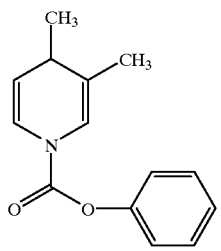
(I-39)
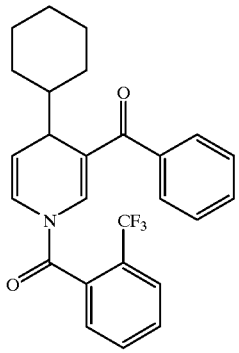
(I-40)
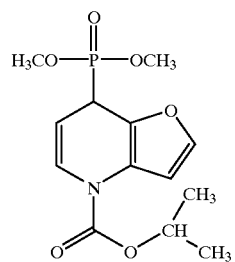
(I-41)
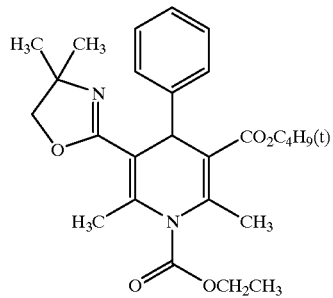
(I-42)
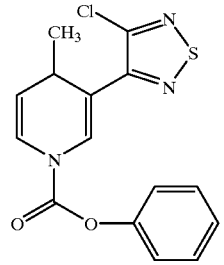

-continued
(I-43)
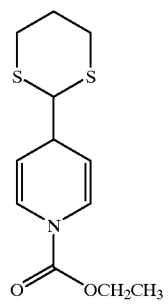
(I-44)
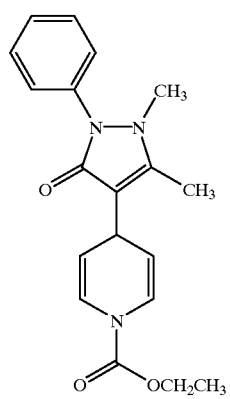
(I-45)
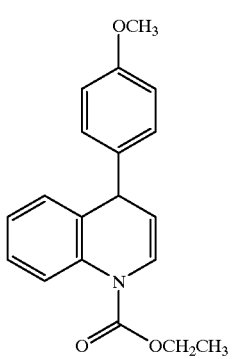
(I-46)
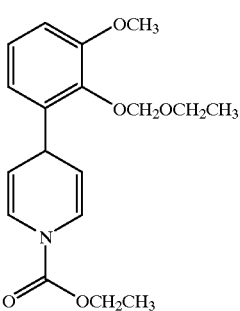
-continued
(I-47)
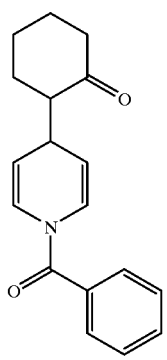
(I-48)
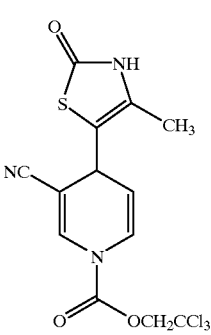
(I-49)
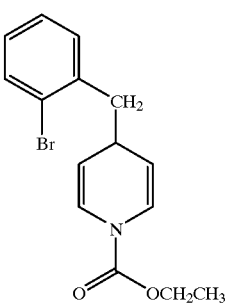
(I-50)
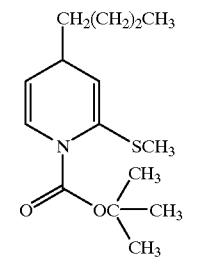
(I-51)
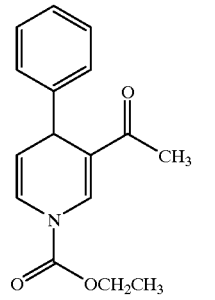

-continued (I-52) (I-57) (I-53) (I-58) (I-54) (I-59) (I-55) (I-60) (I-56) (I-61)

(I-62)
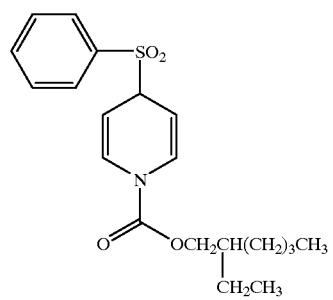
(I-63)
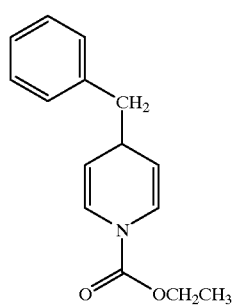
(I-64)
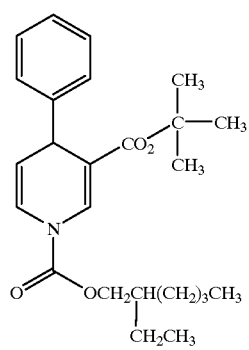
(I-65)
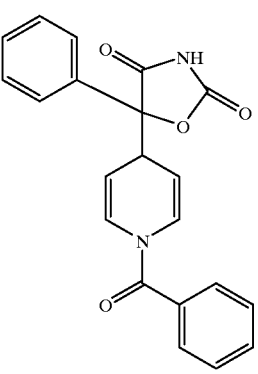
(I-66)
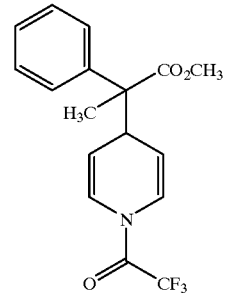
(I-67)
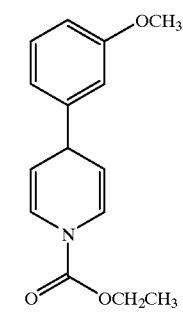
(I-68)
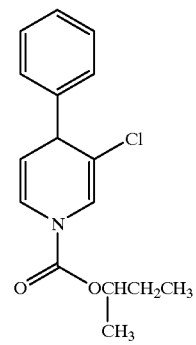
(I-69)
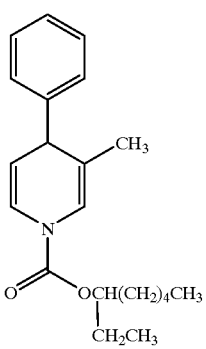
(I-70)
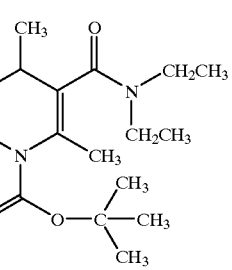

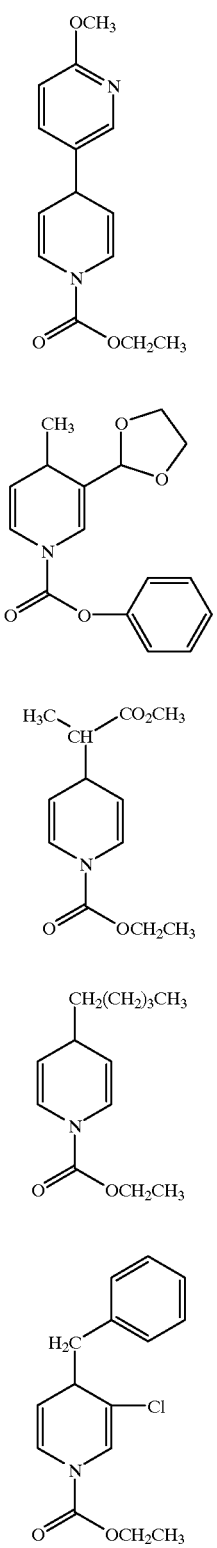
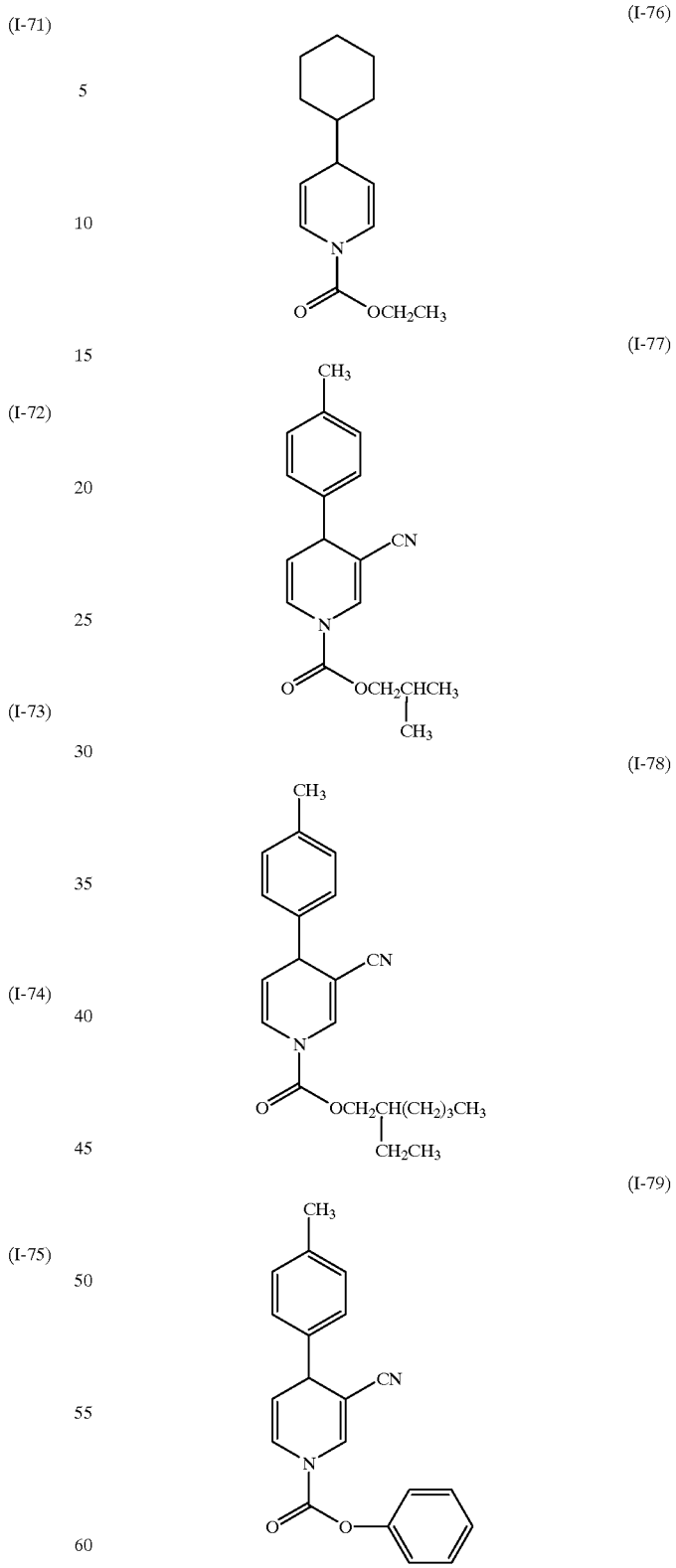
Next, specific examples of the compound represented by formula (II) according to the present invention are shown below. However, the present invention is not limited to these compounds.

(II-1)
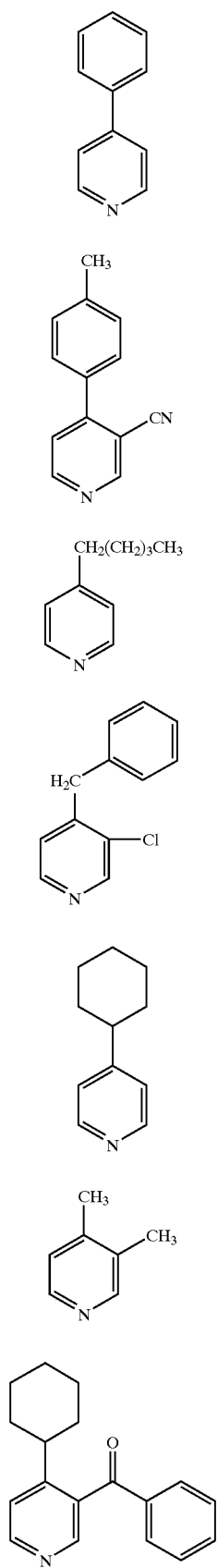
(II-2)
(II-3)
(II-4)
(II-5)
(II-6)
(II-7)
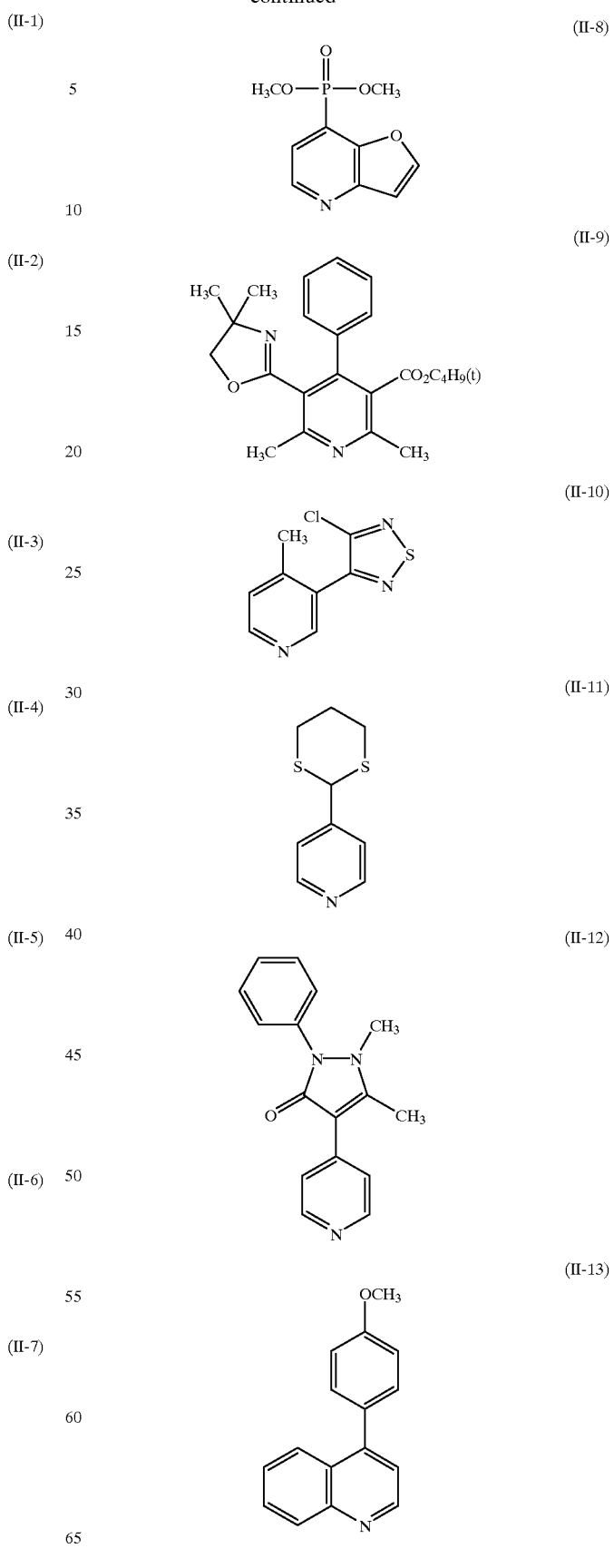
(II-8)
(II-9)
(II-10)
(II-11)
(II-12)
(II-13)

-continued
(II-14) 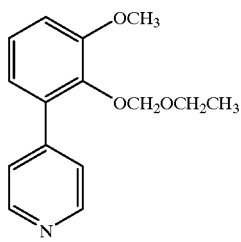
(II-15) 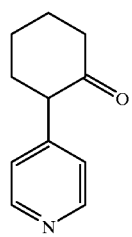
(II-16) 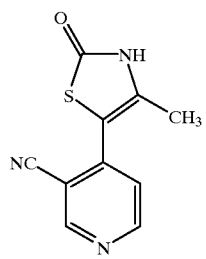
(II-17) 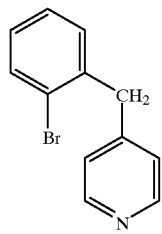
(II-18) 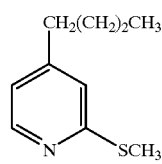
(II-19) 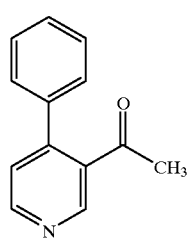
(II-20) 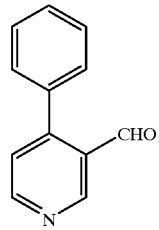
(II-21) 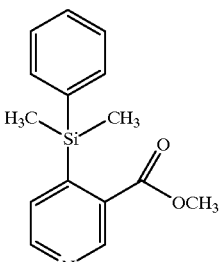
(II-22) 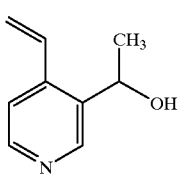
(II-23) 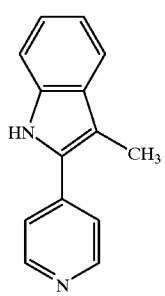
(II-24) 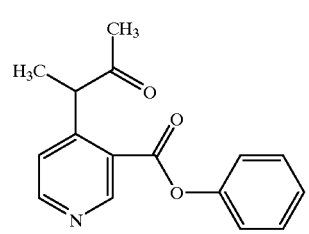
(II-25) 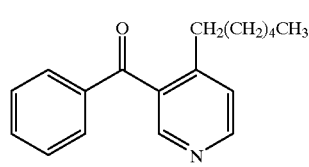

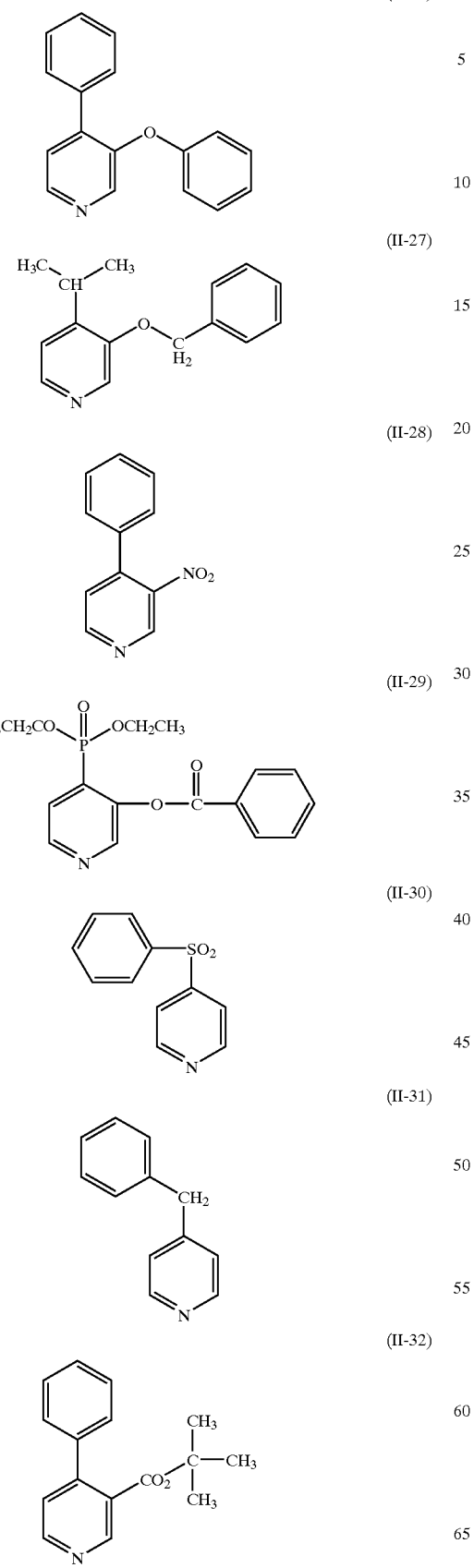
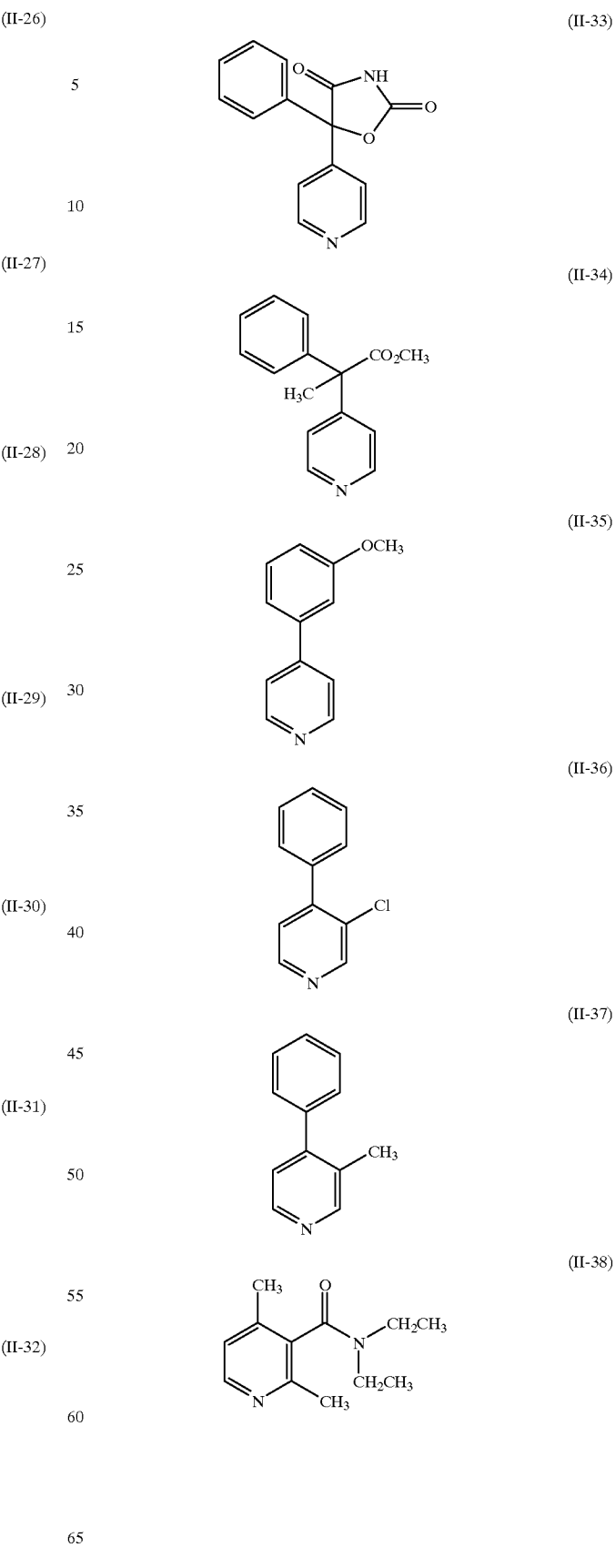

(II-39) 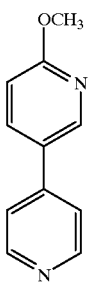

(II-40) 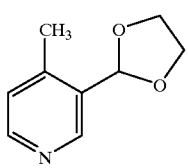

(II-41) 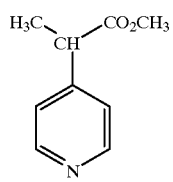

(II-42) 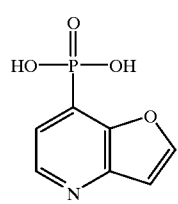

(II-43) 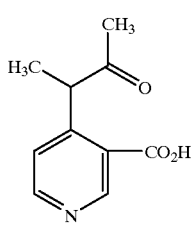

(II-44) 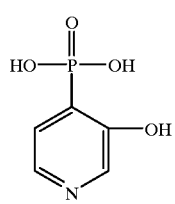

(II-45) 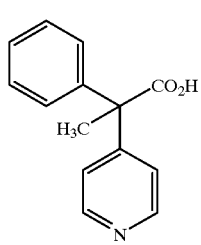

(II-46) 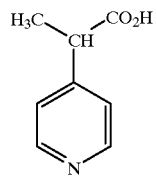

Next, a producing method of the compound represented by formula (II) will be explained in detail.

Various methods for the synthesis of the dihydropyridine compounds represented by formula (I), which are raw materials, are known. For example, they can be advantageously synthesized by an addition reaction of a nucleophilic reagent to a quaternary pyridinium salt (for example, methods as described in J. Org. Chem., 47, 4315–4319 (1982); Heterocycles, 36 (3), 507–518 (1993); ibid. 43 (11), 2425–2434 (1996); ibid. 46, 83–86 (1996); ibid. 48 (12), 2653–2660 (1998); ibid. 51 (4), 737–750 (1999); J. Heterocycl. Chem., 34 (1) 129–142 (1997); Tetrahedron Lett., 40 (22), 4231–4234 (1999); ibid., 40 (22), 4231–4234 (1999); ibid., 40 (34), 6241–6244 (1999); J. Med. Chem., 42 (5), 779–783 (1999); JP-A-10-114743).

The method for producing the compound represented by formula (II) from the aforementioned dihydropyridine compounds represented by formula (I) in the presence of at least one acid, and at least one compound selected from the group consisting of nitrous acid and a nitrite, is explained below in detail.

The acid, which is used in the reaction according to the present invention, may be inorganic acids such as hydrochloric acid, hydrobromic acid, sulfuric acid, nitric acid, and phosphoric acid, or organic acids such as carboxylic acids and sulfonic acids. Two or more of these acids may be used in combination.

The acid is preferably hydrochloric acid, hydrobromic acid, sulfuric acid, and carboxylic acids, and more preferably carboxylic acids. Among carboxylic acids, acetic acid is particularly preferred.

The amount to be added of the acid, which is used in the reaction according to the present invention, is preferably in the range of 1 to 100 times, and more preferably in the range of 1 to 20 times that of the dihydropyridine compound in terms of mole.

In the reaction according to the present invention, at least one compound selected from the group consisting of nitrous acid and a nitrite is used. With respect to the nitrous acid and nitrite, two or more of them may be used in combination. Among nitrous acid and nitrite, an nitrite is preferred.

Similar to the above, two or more of said nitrites may be used in combination. The nitrites are preferably alkali metal nitrites or alkaline earth metal nitrites, more preferably sodium nitrite, potassium nitrite, calcium nitrite, and lithium nitrite, and particularly preferably sodium nitrite and potassium nitrite.

Further, the nitrite may be supplied for the reaction in the solid form, or otherwise may be added in the form of an aqueous solution.

The addition amount of the nitrous acid or nitrite to be used in the reaction according to the present invention, is preferably 1 to 50 times that of the dihydropyridine compound, and more preferably 1 to 15 times that of the dihydropyridine compound, in terms of mole.

The addition order of the raw materials is not particularly limited. However, as a representative procedure, an aqueous solution of a nitrite is added to a solution of a dihydropyridine compound and an acid.

The reaction according to the present invention may be conducted in the absence of a solvent, or otherwise in the presence of a solvent. The solvent to be used in the reaction is not limited, so long as it does not directly participate in the reaction such as substitution reaction and addition reaction, with the compounds represented by formulae (I) and (II). For example, water and organic solvents can be used. Examples of the organic solvents include alcohol (e.g., methanol, ethanol, 2-propanol, n-butanol), ketones (e.g., acetone, methylethyl ketone), esters (e.g., ethyl acetate, methyl acetate, butyl acetate), aliphatic hydrocarbons (e.g., n-pentane, n-hexane, cyclohexane), aromatic hydrocarbons (e.g., toluene, xylene, chlorobenzene), ethers (e.g., diethylether, tetrahydrofuran, dioxane), amides (e.g., N,N-dimethylformamide, N,N-dimethylacetamide, 1-methyl-2-pyrolidone), dimethysulfoxide, sulfolane, acetonitrile, and acetic acid.

Among these solvents, preferred are water, methanol, ethanol, 2-propanol, acetone, methylethyl ketone, ethyl acetate, n-hexane, cyclohexane, toluene, xylene, tetrahydrofuran, N,N-dimethylacetamide, acetonitrile, and acetic acid, more preferably water, methanol, 2-propanol, acetone, ethyl acetate, toluene, acetonitrile, and acetic acid. Further, two or more of these solvents may be used in combination.

Generally, a reaction temperature of the reaction according to the present invention is preferably in the range of −10° C. to 120° C., more preferably in the range of 0° C. to 60° C. Besides, a reaction time differs depending on conditions such as a reaction raw material, a reaction temperature, a reaction concentration, and a reaction scale, but ordinarily in the range of 0.1 to 36 hours, and preferably in the range of 0.5 to 12 hours.

The method for the purification of the pyridine compound according to the present invention is explained below in detail.

After completion of the reaction in the production of the pyridine compound, a crude product of the pyridine compound can be obtained by means of an ordinary method such as crystallization caused by addition to a poor solvent, and a course of operations consisting of extraction, washing, and concentration.

As a method suitable for isolating and purifying a pyridine compound with a high purity from such the crude product, the present inventors have newly found a method in which a crude salt product formed from the pyridine compound and an acid is subjected to an active carbon treatment in a solvent containing water.

Further, the purification method according to the present invention can be applied not only to the pyridine compound obtained by the aforementioned producing method of the present invention, but also to any other pyridine compounds.

The acid to form the crude salt product with the pyridine compound, which salt is used in the purification method according to the present invention, may be inorganic acids such as, hydrochloric acid, hydrobromic acid, sulfuric acid, nitric acid, and phosphoric acid, or otherwise organic acids such as, carboxylic acids, and sulfonic acids. Further, two or more of these acids may be used in combination.

Among these acids, preferred are hydrochloric acid, hydrobromic acid, sulfuric acid, carboxylic acids, and sulfonic acids, more preferably sulfuric acid, carboxylic acids, and sulfonic acids, furthermore preferably sulfuric acid, oxalic acid, succinic acid, methane sulfonic acid, benzene sulfonic acid, and p-toluene sulfonic acid, and particularly preferably sulfuric acid, methane sulfonic acid, and p-toluene sulfonic acid.

An amount of the acid used in the purification method according to the present invention is generally in the range of 0.5 to 50 times, preferably in the range of 0.5 to 20 times, that of the pyridine compound in terms of mole. The crude salt product formed from the pyridine compound and the acid may be subjected to an active carbon treatment once isolated in the solid form. Alternatively, the salt may be subjected to an active carbon treatment omitting such isolation operation.

In the purification method according to the present invention, other solvents may be used in addition to water. As the solvents, preferred are water-soluble solvents, more preferred are methanol, ethanol, 2-propanol, acetone, tetrahydrofuran, and actonitrile, and furthermore preferred are methanol, ethanol, and 2-propanol. Further, two or more of these solvents may be used in combination.

A content of water in these solvents is preferably in the range of 50 to 100%, more preferably in the range of 70 to 100%, and most preferably 100%, that is only water is used as the solvent.

The amount of the solvent containing water, which is used in the purification method according to the present invention, is generally in the range of 0.5 to 100 times, and preferably in the range of 1 to 50 times, that of the pyridine compound in terms of weight part.

The active carbon, which is used in the purification method according to the present invention, is not limited in particular, and articles on the market can be used. The amount of the active carbon used is generally in the range of 0.01 to 10 times, and preferably in the range of 0.01 to 1 time, that of the pyridine compound in terms of weight part.

The temperature of the active carbon treatment in the purification method according to the present invention is generally in the range of 0° C. to 150° C., and preferably in the range of 20° C. to 120° C. The time of the active carbon treatment is generally in the range of 10 minutes to 12 hours, and preferably in the range of 10 minutes to 6 hours. After the active carbon treatment, active carbons are removed by filtration and then, the filtrate is neutralized with a base to isolate a pyridine compound. The base for use in the neutralization may be a hydroxide, carbonate, hydrogen carbonate, phosphate, carboxylate, and alkoxide of an alkali metal or alkaline earth metal. In addition, organic bases such as amines (e.g., ammonia, diethylamine, triethylamine) may be used. Further, two or more of these bases may be used in combination. Among these bases, preferred are a hydroxide, carbonate, and hydrogen carbonate of an alkali metal, and sodium methoxide, ammonia, and more preferred are sodium hydroxide, potassium hydroxide, lithium hydroxide, sodium methoxide, and ammonia.

Next, the method for the producing the pyridine compound represented by formula (II) from the dihydropyridine compound represented by formula (I) in the presence of at least one base, and a hydrogen peroxide solution, is explained in detail.

The base, which is used in the reaction according to the present invention, is not limited in particular, and for example, a hydroxide, carbonate, hydrogen carbonate, phosphate, carboxylate, and alkoxide of an alkali metal or alkaline earth metal may be used. In addition, organic bases such as amines (e.g., ammonia, diethylamine, triethylamine) may also be used. Two or more of these bases may be used in combination.

Among these bases, preferred are a hydroxide, carbonate and hydrogen carbonate of an alkali metal, sodium methoxide, and ammonia, more preferred are sodium hydroxide, potassium hydroxide, lithium hydroxide, sodium carbonate, potassium carbonate, lithium carbonate, sodium methoxide, sodium ethoxide, and ammonia, and particularly preferred are sodium hydroxide, potassium hydroxide, lithium hydroxide, sodium carbonate, potassium carbonate, lithium carbonate, and sodium methoxide.

The amount to be added of the base, which is used in the reaction according to the present invention, is preferably in the range of 1 to 100 times, and more preferably in the range of 1 to 20 times, that of the dihydropyridine compound in terms of mole.

The concentration of a hydrogen peroxide solution, which is used in the reaction according to the present invention, is not limited in particular. Therefore, articles on the market may be used, or otherwise a diluted one may be used. The concentration of the hydrogen peroxide solution used is generally in the range of 1 to 80% by weight, preferably in the range of 3 to 70% by weight, and particularly preferably in the range of 5 to 50% by weight.

The amount to be added of the hydrogen peroxide solution, which is used in the reaction according to the present invention, is an appropriate amount that provides hydrogen peroxide preferably in the range of 1 to 100 times, more preferably in the range of 1 to 20 times, that of the dihydropyridine compound, in terms of mole.

The addition order of the raw materials is not limited in particular. Therefore, a dihydropyridine compound, a solvent, a base, and a hydrogen peroxide solution may be added at the same time. Alternatively, for example, after heating a dihydropyridine compound and a solvent in the presence of a base, a hydrogen peroxide solution may be added.

As in the case for producing the pyridine compound in the presence of an acid, the reaction may be conducted in the presence of a solvent in the case for producing the pyridine compound in the presence of a base. The examples of the organic solvents in the reaction in the presence of a base are those mentioned for the reaction in the presence of an acid, except for an acetic acid is excluded.

Further, among those solvents, preferred are water, methanol, ethanol, 2-propanol, acetone, methylethyl ketone, ethyl acetate, n-hexane, cyclohexane, toluene, xylene, tetrahydrofuran, and acetonitrile, more preferred are water, methanol, ethanol, 2-propanol, acetone, ethyl acetate, toluene, and acetonitrile, and particularly preferred are water, methanol, ethanol, and 2-propanol. Further, two or more of these solvents may be used in combination.

Generally, a reaction temperature of the reaction according to the present invention is preferably in the range of −10° C. to 120° C., and more preferably in the range of 10° C. to 100° C. Besides, a reaction time differs depending on conditions such as a reaction raw material, a reaction temperature, a reaction concentration and a reaction scale, but ordinarily the time is in the range of 0.1 to 36 hours, and preferably in the range of 0.5 to 12 hours.

According to the present invention, it becomes possible to produce a pyridine compound, which is useful for photographic additives, sensitizing dyes, pharmaceuticals, organic EL materials, liquid crystal materials, nonlinear optical materials, and so on, or synthetic intermediates of these materials, by an industrially advantageous method with low cost, high yield and excellent production suitability. Also, it becomes possible to produce such a pyridine compound with a method, which is industrially advantageous and environment-oriented. Further, according to the present invention, it is possible to manufacture a pyridine compound with a high purity, by means of a specific active carbon treatment.

Next, the present invention will be explained in more detail based on examples, but the present invention is not meant to be limited by those examples.

EXAMPLES

Reference Example 1

Synthesis of 1-ethoxycarbonyl-4-phenyl-1,4-dihydropyridine (Compound I-1)

1.9 g (0.01 mole) of CuI was added to a mixture of 18.7 g (0.236 mole) of pyridine and 300 ml of tetrahydrofuran under a $N_2$ atmosphere with stirring. The mixture was stirred at room temperature until the mixture became a homogeneous solution, and thereafter a solution of 22.8 g (0.21 mole) of ethyl chloroformate and 20 ml of tetrahydrofuran was added dropwise, on an ice bath, so that the inner temperature of the reactor could not exceed 20° C. Further, 100 ml of 2M phenyl magnesium chloride solution (0.2 mole; THF solution) was added dropwise over 1.5 hours at the inner temperature ranging from −10° C. to −5° C. The reaction mixture was stirred for 0.5 hours at the temperature of −10° C. to −5° C. Further, after stirring for 1 hour at 25° C., about 150 ml of tetrahydrofuran was removed from the mixture by a vacuum distillation, and then 180 ml of aqueous 20% ammonium chloride solution was added to the resultant mixture. The reaction product was extracted with 180 ml of ethyl acetate, and then the aqueous layer was discharged. Thereafter, 180 ml of 10% hydrochloric acid was added and stirred for 15 minutes. The resulting precipitate was removed by filtration through celite, and then the celite was washed with 40 ml of ethyl acetate. After removing the aqueous layer of the filtrate, the organic layer was washed once with 180 ml of 10% hydrochloric acid, and twice with 180 ml each of water. The organic layer was concentrated under a reduced pressure to obtain Compound I-1: obtained amount 44.6 g; purity 88.0% (determined by HPLC); yield 85.5%.

Example 1

Synthesis and Purification of 4-phenylpyridine (Compound II-1)

To a mixture of 10.0 g (0.038 mole) of Compound I-1 obtained in <Reference Example 1> and 13.9 g (0.232 mole) of acetic acid, an aqueous solution of 7.9 g (0.114 mole) of sodium nitrite dissolved in 12 ml of water, was added dropwise over 1 hour, on an ice bath, so that the inner temperature of the reactor could not exceed 20° C. After completion of dropping, the reaction mixture was stirred for 2 hours at the inner temperature of 25° C. Thereafter, 25 ml of water was added to the mixture, and then, 25% aqueous ammonia was added dropwise, so that the pH of the reaction solution became within the range of 6 to 7 and the inner temperature could not exceed 40° C. 25 ml of ethyl acetate was added to the mixture, and stirred for 30 minutes. After removing the aqueous layer, the organic layer was washed twice with 40 ml each of water. After conducting concentration of the organic layer under a reduced pressure, the residue was dissolved in 30 ml of 2-propanol. With stirring the mixture, 4.1 g (0.0418 mole) of concentrated sulfuric acid was added dropwise, so that the inner temperature could not exceed 30° C. After stirring the mixture at room temperature for 30 minutes, and then at 10° C. or less for 30 minutes, the precipitate of 4-phenylpyridine sulfate was collected by filtration, and then washed with 20 ml of cooled 2-propanol. The precipitate was mixed with 50 ml of water, and 0.9 g of active carbon was added. The mixture was heated under reflux for 1 hour, and then filtrated through celite. The celite was then washed with 20 ml of water. The pH of the filtrate was adjusted to the range of 7 to 8 with aqueous 25% sodium hydroxide solution. After stirring at 20° C. for 1 hour, the precipitated crystals were collected by filtration under a reduced pressure, and washed and dried. A white crystal of Compound II-1 was obtained: obtained amount 4.5 g; yield 76.3%; purity 100% (determined by HPLC).

The structure of the intended Compound II-1 was identified by $^1$H-NMR.

| $^1$H-NMR (300 MHz; Solvent CDCl$_3$; Internal Standard: TMS) | |
|---|---|
| δ ppm | 7.5 (m, 5H) |
| | 7.65 (d, 2H) |
| | 8.65 (d, 2H) |

Besides, in the aforementioned purification using an active carbon, the active carbon treatment was also conducted with 50 ml of methanol in place of 50 ml of water. However, it was impossible to remove a brown colored material.

Example 2

To a mixture of 10.0 g (0.038 mole) of Compound I-1 obtained in <Reference Example 1> and 13.9 g (0.232 mole) of acetic acid, an aqueous solution of 7.9 g (0.114 mole) of sodium nitrite dissolved in 12 ml of water, was added dropwise over 1 hour, on an ice bath, so that the inner temperature of the reactor could not exceed 20° C. After completion of dropping, the reaction mixture was stirred for 2 hours at the inner temperature of 25° C. Thereafter, 25 ml of water was added to the mixture, and 25% aqueous ammonia was added dropwise, so that the pH of the reaction solution became within the range of 6 to 7 and the inner temperature could not exceed 40° C. To the mixture, 25 ml of ethyl acetate was added, and stirred for 30 minutes. After removing the aqueous layer, the organic layer was washed twice with 40 ml each of water. The organic layer was extracted twice with 10% hydrochloric acid. The pH of the combined aqueous layers were adjusted to the range of 7 to 8, with aqueous 25% sodium hydroxide solution. After stirring at 20° C. for 1 hour, the precipitated crude crystals were collected by filtration under a reduced pressure. Washing and drying gave Compound II-1 as a brown crude crystal: obtained amount 5.8 g; purity 85.0% (determined by HPLC); yield 83.6%.

Reference Example 2
Synthesis of 1-isobutyloxycarbonyl-4-phenyl-1,4-dihydropyridine (Compound I-2)

1.9 g (0.01 mole) of CuI was added to a mixture of 18.7 g (0.236 mole) of pyridine and 150 ml of tetrahydrofuran under a N$_2$ atmosphere, with stirring. The mixture was stirred at room temperature until the mixture became a homogeneous solution, and thereafter a solution of 28.7 g (0.21 mole) of isobutyl chloroformate and 20 ml of tetrahydrofuran was added dropwise, on an ice bath, so that the inner temperature of the reactor could not exceed 20° C. Further, 100 ml of 2M phenyl magnesium chloride solution (0.2 mole; a THF solution) was added to the mixture dropwise, over 1 hour, at the inner temperature of 0±3° C. (i.e., −3° C. to 3° C.). The mixture was stirred for 20 minutes at the temperature of 0±3° C., and further stirred for 1 hour 25° C. After removing about 60 ml of tetrahydrofuran by vacuum distillation, 180 ml of toluene was added, and then 60 g (0.061 mole) of 10% sulfuric acid was added dropwise. The resulting precipitate was removed by filtration through celite, and then the celite was washed with 40 ml of toluene. After removing the aqueous layer of the filtrate, the organic layer of the filtrate was washed twice with 180 ml each of 10% hydrochloric acid, and twice with 180 ml each of water. The organic layer was concentrated under a reduced pressure to obtain Compound I-2: obtained amount 51.0 g; purity 86.0% (determined by HPLC); yield 85.2%.

Example 3
Synthesis and Purification of 4-phenylpyridine (Compound II-1)

The reaction and purification were conducted on the same conditions as in EXAMPLE 1, except that 9.8 g (0.038 mole) of Compound I-2 obtained in <Reference Example 2> was used as a dihydropyridine compound. As a result, Compound II-1 was obtained as a white crystal: obtained amount 4.4 g; yield 74.6%; purity 99.9% (determined by HPLC).

The structure of the desired compound, Compound II-1, was identified by $^1$H-NMR.

Reference Example 3
Synthesis of 1-(2-ethylhexyloxycarbonyl)-4-phenyl-1,4-dihydropyridine (Compound I-3)

The synthesis was carried out on the same conditions as in EXAMPLE 2, except that 40.5 g (0.21 mole) of 2-ethylhexyl chloroformate was used as acid chloride. As a result, Compound I-3 was obtained, in an amount of 63.1 g, with 83.0% purity (determined by HPLC) and 83.5% yield.

Example 4

2 g (6.38 mmol) of Compound I-3 synthesized in <Reference Example 3> and 1.53 g (25.52 mmol) of acetic acid were mixed, and to the mixture, an aqueous solution of sodium nitrite 880 mg (12.76 mmol) in 2 ml of water was added dropwise, over 30 minutes, on an ice bath, so that the inner temperature of the reactor could not exceed 20° C. After completion of dropping, the reaction mixture was stirred for 3 hours at the inner temperature of 25° C. Thereafter, the mixture was extracted with ethyl acetate, washed and concentrated. The 4-phenylpyridine content in the concentrated product was determined by HPLC. Yield 93%.

Comparative Examples 1 to 5

The reactions were conducted with utilizing 2 g (6.38 mmol) of Compound I-3 synthesized in <Reference Example 3>, and utilizing respective oxidants and solvents shown in Table 1, in place of sodium nitrite and acetic acid used in EXAMPLE 4. The oxidations were carried out on the conditions shown in Table 1. Thereafter, each of the reaction mixture was extracted with ethyl acetate, washed, and concentrated. The 4-phenylpyridine content in each of the concentrated products was determined by HPLC. The results are shown in Table 1. For reference, in Table 1, the result in EXAMPLE 4 is also described, together with the results of Comparative Examples 1 to 5.

TABLE 1

| | Oxidant (equivalent weight) | Solvent | Reaction temperature | Hour | Yield |
|---|---|---|---|---|---|
| Comparative | Air | — | 50° C. | 6 hours | 15% |

TABLE 1-continued

| example 1 | | | | | |
|---|---|---|---|---|---|
| Comparative example 2 | Sulfur (1) | xylene | 140° C. | 6 hours | 90% |
| Comparative example 3 | 5% Pd/C (1 mol %) | toluene/ H₂O | 110° C. | 6 hours | 14% |
| Comparative example 4 | 31% H₂O₂ (2.6) | MeOH | 50° C. | 3 hours | 4% |
| Comparative example 5 | FeSo₄ catalyst + 31% H₂O₂ (1.1) | MeOH | 25° C. | 10 hours | 53% |
| Example 4 | NaNo₂ (2) | AcOH | 25° C. | 3 hours | 93% |

As is apparent from Table 1, it is understood that the reaction proceeded at an ordinary temperature and further gave an intended product with a high yield in EXAMPLE 4 according to the present invention. In contrast, the yields were as low as the range of 4 to 53% in Comparative Examples 1, 3 to 5. Further, Comparative Example 2 had a drawback that the reaction did not proceed unless the reaction temperature was high, and therefore these Comparative Examples 1 to 5 were disadvantageous from the viewpoints of working operation and cost.

Reference Example 4
Synthesis of 1-(2-ethylhexyloxycarbonyl)-4-phenyl-1,4-dihydropyridine (Compound I-3)

1.9 g (0.01 mole) of CuI was added to a mixture of 18.7 g (0.236 mole) of pyridine and 150 ml of tetrahydrofuran under a $N_2$ atmosphere, with stirring. The mixture was stirred at room temperature until the mixture became a homogeneous solution, and thereafter a solution of 40.5 g (0.21 mole) of ethylhexyl chloroformate and 20 ml of tetrahydrofuran was added to the mixture, dropwise, on an ice bath, so that the inner temperature of the reactor could not exceed 20° C. Further, 100 ml of 2M phenyl magnesium chloride solution (0.2 mole; THF solution) was added to the mixture, dropwise, over 1 hour, at the inner temperature of 0±3° C. The reaction mixture was stirred at 0±3° C. for 20 minutes, and further stirred at 25° C. for 1 hour. After removing about 60 ml of tetrahydrofuran by vacuum distillation, 180 ml of toluene was added to the resultant, and 60 g (0.061 mole) of 10% sulfuric acid was added dropwise. The resulting precipitate was removed by filtration through celite, and then the celite was washed with 40 ml of toluene. After removing the aqueous layer of the filtrate, the organic layer of the filtrate was washed twice with 180 ml each of 10% hydrochloric acid, and twice with 180 ml each of water. The organic layer was concentrate under a reduced pressure to obtain Compound I-3: obtained amount 63.1 g; purity 83.0% (determined by HPLC); yield 83.5%.

Example 5
Synthesis and Purification of 4-phenylpyridine (Compound II-1)

52.9 g (0.14 mole) of Compound I-3 obtained in <Reference Example 4> and 16.8 g (0.42 mole) of sodium hydroxide were dissolved in 90 ml of methanol, and then stirred at 60° C. for 1 hour, allowed to cool down to 30° C. Thereafter, 39.5 g (0.36 mole) of 31% hydrogen peroxide solution was added. At this time, the inner temperature elevated to about 35° C. After reaction at 50° C. for 3 hours, 100 ml of toluene, and an aqueous solution of 50 g (0.40 mole) of sodium sulfite dissolved in 150 ml of water, were added. After stirring, the aqueous layer was removed, and the organic layer was washed twice with 100 ml of water at each time. The resulting organic layer was extracted twice with 100 ml of 10% hydrochloric acid at each time. The combined aqueous layers were adjusted to the pH of 7 to 8 with aqueous 25% sodium hydroxide solution. After stirring at 20° C. for 1 hour, the produced crude crystals were collected by filtration under a reduced pressure, and washed and dried, to obtain Compound II-1 as a white crystal: obtained amount 15.2 g; HPLC area purity 99.7%; yield 70.0%.

The structure of the intended compound, Compound II-1, was identified by ¹H-NMR.

| ¹H-NMR (300 MHz; Solvent CDCl₃; Internal Standard: TMS) | |
|---|---|
| δ ppm | 7.5 (m, 5H) |
| | 7.65 (d, 2H) |
| | 8.65 (d, 2H) |

Comparative Example 6

To a solution of 2 g (6.38 mmol) of Compound I-3 synthesized in <Reference Example 4> that was dissolved in 4 ml of methanol, was added 1.8 g (16.4 mmol) of 31% hydrogen peroxide solution. After reaction at 50° C. for 3 hours, 10 ml of ethyl acetate, and 10 ml of a saturated sodium sulfite aqueous solution, were added. After stirring, the aqueous layer was removed. 100 mg (0.648 mmol) of biphenyl as the Internal Standard of HPLC was added to the organic layer, and stirred to dissolve it. Quantitative analysis by HPLC gave 4% yield of 4-phenylpyridine.

Having described our invention as related to the present embodiments, it is our intention that the invention not be limited by any of the details of the description, unless otherwise specified, but rather be construed broadly within its spirit and scope as set out in the accompanying claims.

What we claim is:
1. A method for producing a pyridine compound represented by formula (II), comprising oxidizing a dihydropyridine compound represented by formula (I) (i) in the presence of at least one acid and at least one compound selected from the group consisting of nitrous acid and a nitrate, or (ii) in the presence of at least one base, and a hydrogen peroxide solution:

Formula (I)

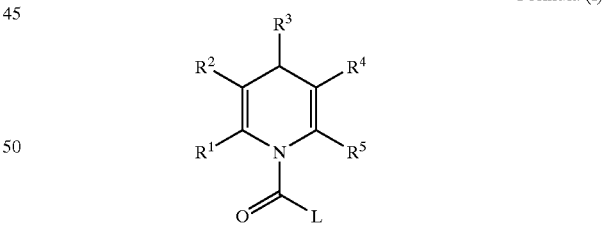

wherein each of $R^1$, $R^2$, $R^3$, $R^4$, and $R^5$ independently represents a hydrogen atom, a halogen atom, an alkyl group, an aryl group, an alkenyl group, a cyano group, a formyl group, a carboxyl group, an alkoxycarbonyl group, an aryloxycarbonyl group, a substituted or unsubstituted carbamoyl group, an alkyl carbonyl group, an arylcarbonyl group, a nitro group, a substituted or unsubstituted amino group, an acylamino group, a sulfonamido group, an imido group, an imino group, a hydroxyl group, an alkoxy group, an aryloxy group, an acyloxy group, an alkylsulfonyloxy group, an arylsulfonyloxy group, a sulfo group, a substituted or unsubstituted sulfamoyl group, an alkylthio group, an arylthio group, an alkylsulfonyl group, an arylsulfonyl group, a silyl group, a phosphoryl group, or a heterocyclic group; L represents an alkyl group, an alkoxy group, an aryl group, or an aryloxy group, each of which may have a substituent:

Formula (II)

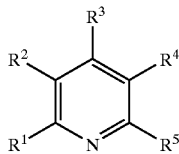

wherein each of $R^1$, $R^2$, $R^3$, $R^4$, and $R^5$ has the same meanings as those of formula (I).

2. The method for producing a pyridine compound as claimed in claim 1, wherein the oxidization is conducted in the presence of at least one acid and at least one compound selected from the group consisting of nitrous acid or a nitrite.

3. The method for producing a pyridine compound as claimed in claim 2, wherein said acid is a carboxylic acid.

4. The method for producing a pyridine compound as claimed in claim 2, wherein said nitrite is an alkali metal nitrite or an alkaline earth metal nitrite.

5. The method for producing a pyridine compound as claimed in claim 2, wherein each of $R^1$, $R^2$, $R^4$ and $R^5$ represents a hydrogen atom, and $R^3$ represents an aryl group in formula (I) and formula (II), respectively.

6. The method for producing a pyridine compound as claimed in claim 1, wherein the oxidization is conducted in the presence of at least one base, and a hydrogen peroxide solution.

7. The method for producing a pyridine compound as claimed in claim 6, wherein said base is an inorganic base, or an alkoxide of an alkali metal or alkaline earth metal.

8. The method for producing a pyridine compound as claimed in claim 6, wherein each of $R^1$, $R^2$, $R^4$, and $R^5$ in formulae (I) and (II) is a hydrogen atom.

9. The method for producing a pyridine compound represented by formula (II) as claimed in claim 1, wherein each of $R^1$, $R^2$, $R^3$, $R^4$, and $R^5$ independently represents a hydrogen atom, a halogen atom, an alkyl group, an aryl group, a cyano group, a formyl group, an alkoxycarbonyl group, an aryloxycarbonyl group, a substituted or unsubstituted carbamoyl group, an alkyl carbonyl group, an arylcarbonyl group, an alkoxy group, an aryloxy group, an acyloxy group, or a heterocyclic group.

10. The method for producing a pyridine compound as claimed in claim 1, wherein the oxidization is carried out at the temperature of −10° C. to 120° C.

11. The method for producing a pyridine compound as claimed in claim 2, wherein the oxidization is carried out at the temperature of 0° C. to 60° C.

12. The method for producing a pyridine compound as claimed in claim 6, wherein the oxidization is carried out at the temperature of 10° C. to 100° C.

13. The method for producing a pyridine compound as claimed in claim 2, wherein the amount of the acid is 1 to 100 times that of the dihydropyridine compound in terms of mole.

14. The method for producing a pyridine compound as claimed in claim 2, wherein the amount of the nitrous acid or nitrite is 1 to 50 times that of the dihydropyridine compound in terms of mole.

15. The method for producing a pyridine compound as claimed in claim 6, wherein the amount of the base is in the range of 1 to 100 times that of the dihydropyridine compound in terms of mole.

16. The method for producing a pyridine compound as claimed in claim 6, wherein the amount of the hydrogen peroxide solution is an appropriate amount that provides hydrogen peroxide in the range of 1 to 100 times that of the dihydropyridine compound, in terms of mole.

17. The method for producing a pyridine compound represented by formula (II) as claimed in claim 1, wherein each of $R^1$, $R^2$, $R^3$, $R^4$, and $R^5$ independently represents a hydrogen atom, a halogen atom, an alkyl group, an aryl group, an alkenyl group, a cyano group, a formyl group, a carboxyl group, an alkoxycarbonyl group, an aryloxycarbonyl group, a substituted or unsubstituted carbamoyl group, an alkyl carbonyl group, an arylcarbonyl group, a nitro group, a hydroxyl group, an aryloxy group, an acyloxy group, an alkylthio group, an arylsulfonyl group, a silyl group, a phosphoryl group, or a heterocyclic group.

18. The method for producing a pyridine compound represented by formula (II) as claimed in claim 1, wherein $R^3$ is an aryl group.

* * * * *